United States Patent [19]
Johnson

[11] Patent Number: 4,884,454
[45] Date of Patent: Dec. 5, 1989

[54] MANBASKET TESTING APPARATUS AND METHOD

[75] Inventor: Roy L. Johnson, Oregon City, Oreg.

[73] Assignee: Lifting Technologies, Inc., Missoula, Mont.

[21] Appl. No.: 270,207

[22] Filed: Nov. 14, 1988

[51] Int. Cl.⁴ .............................................. G01N 3/00
[52] U.S. Cl. ..................................... 73/788; 73/865.6
[58] Field of Search .................. 73/788, 865.6, 865.9, 73/789, 849; 182/63

[56] References Cited

U.S. PATENT DOCUMENTS 4,660,678  4/1987  Krag ................................. 182/63 X

FOREIGN PATENT DOCUMENTS 2148517  5/1985  United Kingdom ................. 73/849

Primary Examiner—Jerry W. Myracle
Attorney, Agent, or Firm—William D. West

[57] ABSTRACT

A manbasket testing apparatus for use in the trial lift and proof testing of personnel work platforms known as manbaskets is disclosed. The testing device provides a manbasket supported by a floor attached sling and providing a removable test weight attached through and underneath the floor of the manbasket by the use of eyebolts attached to the test weight and extending through the floor with attachment rods slid transversely through the eyebolts. A method of testing using the manbasket testing apparatus is also disclosed.

13 Claims, 4 Drawing Sheets

MANBASKET TESTING APPARATUS AND METHOD

BACKGROUND OF THE INVENTION

1. Field of the invention

This invention relates to a suspended work platform testing apparatus and a method of load testing a work platform suspended from a crane.

2. Discussion of the Technical Problems

Work platforms known as manbaskets are small platforms or stages within which workmen can be transported vertically to worksites. Generally, such manbaskets are suspended from cranes or derricks and are hoisted by the crane or derrick to position workers at the worksite.

Although cranes are material handling devices, manbaskets are used extensively due to their low cost, flexability, speed, and convenience. Such use raises safety issues and invites regulations regarding suspended manbaskets.

Cranes have different boom lengths and extensions so that for any given setup having a set boom length and angle of boom placement, only a certain amount of weight can be carried in the manbasket.

In order to ensure that the operation of the crane is safe, a proof load test and trial lift is required by the Occupational Safety and Health Administration (OSHA). OSHA also mandates a manufacturing requirement that the platform must be designed to support five times the maximum intended load (including the workers as well as associated light tools). In addition, separate load tests must be used whenever repairs are made to the platform. Effective Oct. 3, 1988, OSHA has amended its standards for cranes and derricks as found in 29 C.F.R. 1926.550 by prohibiting the use of cranes or derricks to hoist personnel except in the situation where no safe alternative is possible and as long as a number of requirements are met. These requirements include that a trial lift with the unoccupied personnel platform loaded at least to the anticipated lift weight shall be made from ground level or any other location where employees will enter the platform to each location at which the personnel platform is to be hoisted in position. This trial lift shall be performed immediately prior to placing personnel on the platform. A single trial lift may be performed at one time for all locations that are to reached from a single setup position. Additionally, at each job site prior to hoisting any employees on the personnel platform and after any repair modification, the platform and rigging shall be proof tested to 125 percent of the platform's rated capacity by holding it in a suspended position for five minutes with the test load evenly distributed on the platform. Such nondestructive field testing provides the necessary assurance that any defect in the platform or rigging would be detected and corrected before any personnel were hoisted.

The OSHA requirements thus include both a proof test to test the capacity and construction of the personnel platform and also a trial lift to determine that the lifted route is free of obstacles, to determine work location accessibility, to confirm that no work locations will place the crane or derrick in such a configeration where the intended load would exceed the 50 percent limit of the crane's rated capacity, to ensure soil or other supporting surface stability and to determine suitability for the intended lift. The proof test and trial lift can be conducted simultaneously.

In order to provide the testing as required by OSHA, it has been found that sandbags, metal weights, and other objects with known weight can be employed by placing them in the manbasket. Unfortunately, the movement of hundreds and thousands pounds of material on and off the manbasket is difficult, time consuming, and in itself a dangerous activity. The constant testing mandated by OSHA which is intended to provide safety for the workers would be greatly enhanced if there existed a convenient apparatus for attaching test weights to the manbasket. Such a device should employ weight of a known value and should be attached to the manbasket in a secure manner to evenly distribute the weight and yet be quickly released or attached as needed.

Since a crane easily lifts the manbasket vertically, it would be most convenient if the manbasket were made so it could be placed over a known weight. The weight could then be securely attached to the manbasket and both the proof testing as well as the trial lift could be conducted.

No known examples of manbasket testing devices have been discovered. Very few devices in the known art relate to testing of cranes, cables, and the like and none known are directed to providing a manbasket testing apparatus and method.

Accordingly, a need exists for a manbasket testing apparatus that would provide a safe, convenient work platform while in use and yet the testing device could be easily detached for testing to comply with government safety regulations. Such a device should be easily repaired, not subject to damage by proper use, and simple to manufacture. The instant invention is directed to all these needs as well as to others as explained in the following summary.

SUMMARY OF THE INVENTION

It is a feature of the invention to provide a manbasket testing device.

It is another feature of the instant invention to provide a manbasket testing apparatus having a detachable trial lift and proof test weight.

It is another feature of the instant invention to provide a method of proof testing and trial lift testing of work.platforms and manbaskets.

These and other features and objects are attained according to the instant invention by providing a crane suspended manbasket or work platform with an easily detachable prelift test weight. The manbasket is of a conventional box-type construction, however, a pretested attachment sling is removably attached to the floor of the manbasket. A large rectangular weight, preferably metal, is slung underneath the floor of the manbasket and is held securely to the floor of the manbasket by rods extending through eyebolts rigidly affixed to the test weight. The eyes of the eyebolts are inserted into slots in the floor of the manbasket where attachment rods are run through the eyes and secured by a key lock. The testing weight is provided with an outwardly and downwardly projecting support skid. The manbasket floor is elevated by a support skid. The manbasket is lowered entirely over the test weight where the weight can be removably attached to the manbasket. When not used for lifting personnel, the work platform and testing weight can be stored together and transported in an attached relationship.

BRIEF DESCRIPTION OF THE DRAWINGS

The advantages of this invention will become apparent upon consideration of the following detailed disclosure of the invention, especially when taken in conjunction with the accompanying drawings, wherein.

DESCRIPTION OF THE PREFERRED EMBODIMENT

Figure 1:
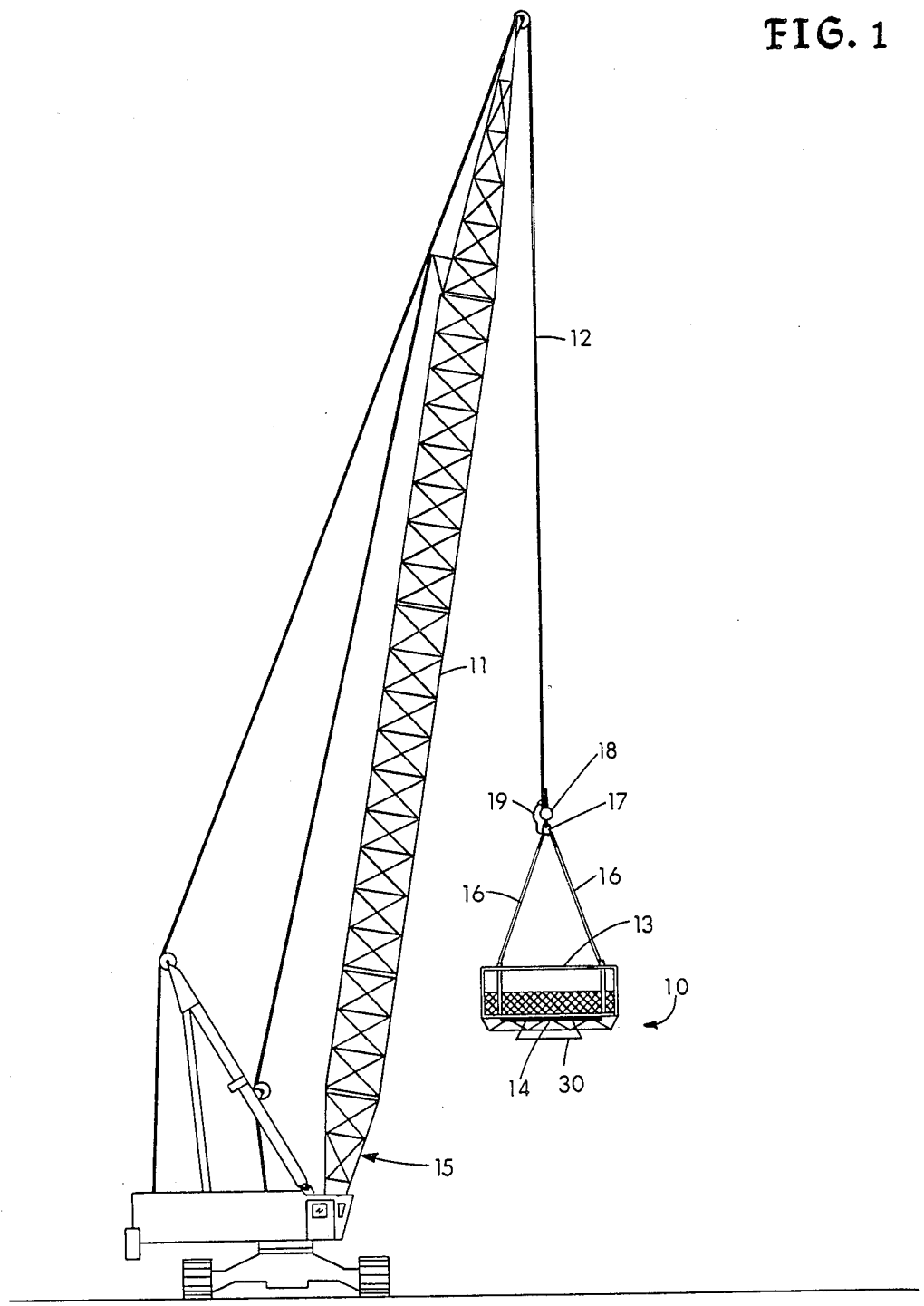
FIG. 1 is a front elevational view of a crane and a work platform and a manbasket attached to the crane in a testing configuration with the testing weight attached to the manbasket in accordance with the present invention.

The manbasket testing apparatus 10 of the instant invention is depicted generally in FIG. 1. As can be seen by reference to FIG. 1, the invention 10 is suspended from a crane 15 having a boom 11 and suspension cable 12. Invention 10 provides a manbasket 13 and a test weight 14 attached underneath manbasket 13. Sling cables 16 attach manbasket 13 to crane suspension cable 12 by use of master link 17, ball 18, and safety connection 19.

Figure 2:
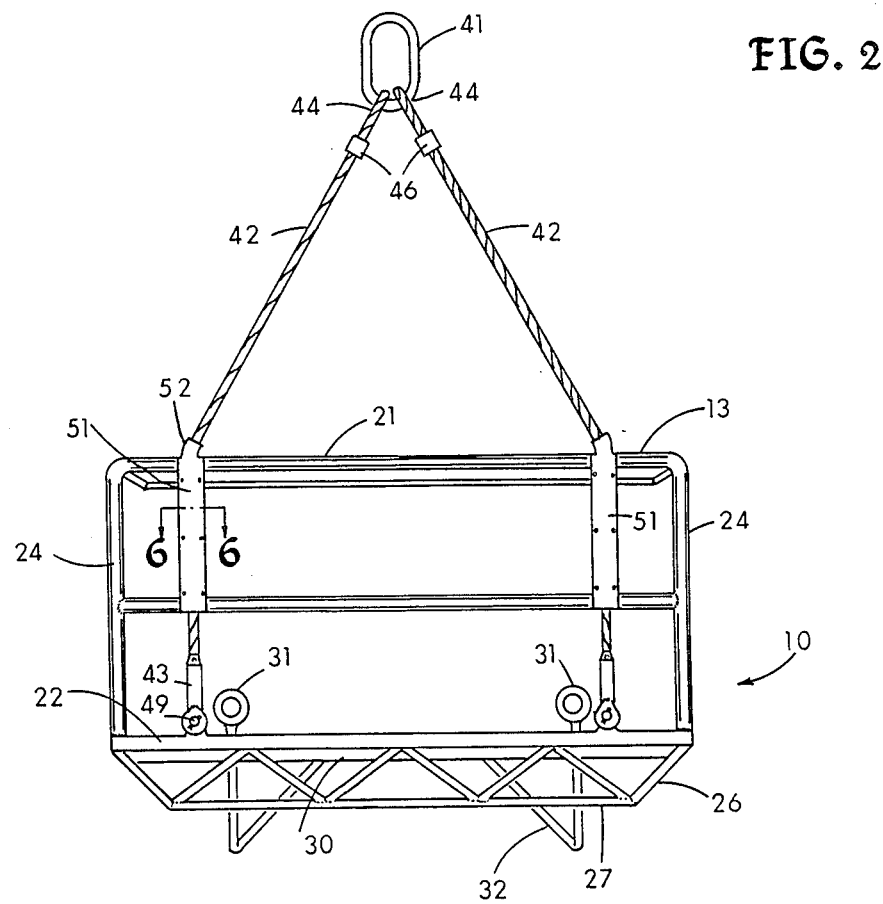
FIG. 2 is a side elevational view of the manbasket cradled over a test weight.
Figure 3:
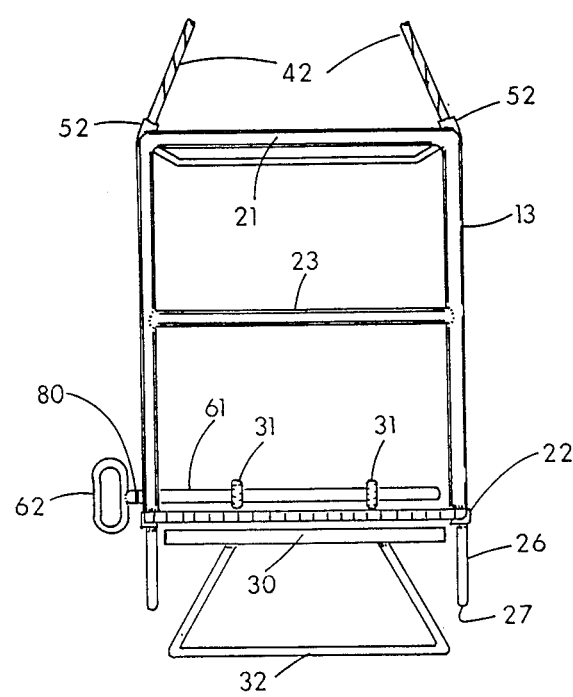
FIG. 3 is an end elevational view of the manbasket stradling a test weight with an attachment pin securing the test weight to the manbasket in accordance with the present invention.
Figure 4:
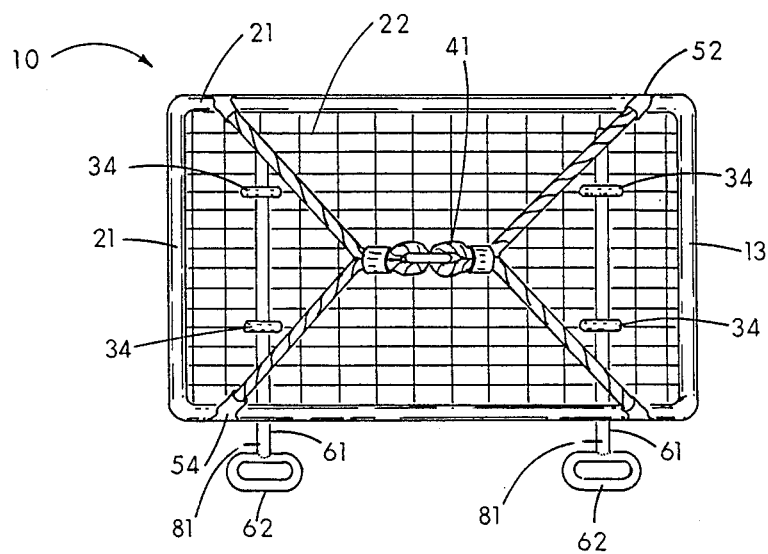
FIG. 4 is a top plan view of the manbasket and attaching sling with the pins inserted through the test weight eyes and with the key lock engaged.

Although the environment in which the invention 10 is utilized is depicted in FIG. 1, a more detailed view of the invention 10 can be seen with reference to FIGS. 2, 3, and 4. As can be seen by reference to FIG. 2, manbasket 13 is a generally rectangular welded frame or box having upper handrails 21, floor 22, middle handrails 23, and corner upright supports 24. A pair of parallel support skid trusses 26 are attached to floor 22 to provide a resting surface 27 when the manbasket is placed upon the ground or other flat surface when transporting personnel.

Continuing with reference to FIG. 2, it can be seen that test weight 30 is located underneath and adjacent to floor 22. Test weight 30 is provided with eye bolts 31 extending upwardly from test weight 30 and attached securely thereto and having the eyes of the eyebolts arranged so as to provide a passageway for insertion of an attachment pin. Test weight 30 could be of any size and weight depending upon the test weight required for the size of the manbasket. Manbaskets are designed for one or more persons and the test load requirements differ with the different manbasket configuration. It is assumed that the test weight would be in accordance with the then existing OSHA requirements. The test weight 30 is generally a right rectangular block made of a homogenous material having a known weight such as mild steel, cast iron, or the like. As can be seen by reference to FIGS. 2 and 3, test weight 30 is further provided with a support stand 32 below test weight 30 which allows test weight 30 to be placed upon a flat surface such as the ground to be in proper position and elevated sufficiently for attachment to manbasket 13 when used in the testing configuration.

Continuing with reference to FIG. 2, it can be seen that manbasket 13 is slung from the crane by the use of master link 41 and manbasket slings 42. Sling 42 is provided with a swaged fitting 43 having a clevis for attachment to floor 22 of manbasket 13 in a manner well known in the art. In order to route the cable of sling 42 from floor 22 up to attachment ring 41, the cable must be spaced and routed freely without kinking or bending. The correct routing of sling 42 is accomplished by the use of fairlead 51 providing a channel rigidly attached to handrails 21 and 23 and a smooth elbow 52 to protect sling cable 42. Upper end 44 of sling 42 is provided with a cable thimble and fitting 46 to make a secure, safe sling assembly. The sling assembly is pretested so that safety is not compromised.

With reference to FIG. 3, it can be seen that the eyes 31 of the eyebolts attached to test weight 30 are aligned so as to allow the insertion of attachment pin 61. Attachment pin 61 is an elongate rod having a convenient handle 62 and key lock to secure rod. When eyebolts 31 extend through slots in floor 22 of manbasket 13 then attachment pin 61 can be inserted through eyebolts 31 to hold test weight 30 in a fixed position underneath the floor 22 of manbasket 13. The pin 61 rests upon floor 22 and supports weight 30 through eyebolts 31 when suspended from sling 42. Key tab 81 on rod 61 is engaged so that attachment rod 61 will not inadvertently be removed.

With reference to FIG. 4, it can seen that manbasket 13, when in the test weight attached position, provides slots 34 through which test weight eyes 31 extend upwardly and through the floor to a position whereby elongate rods 61 can be inserted to hold test weight 30 securely to the underside of floor 22 to provide a prelift testweight. The key lock 80 secures rod 61 in place.

Figure 5:
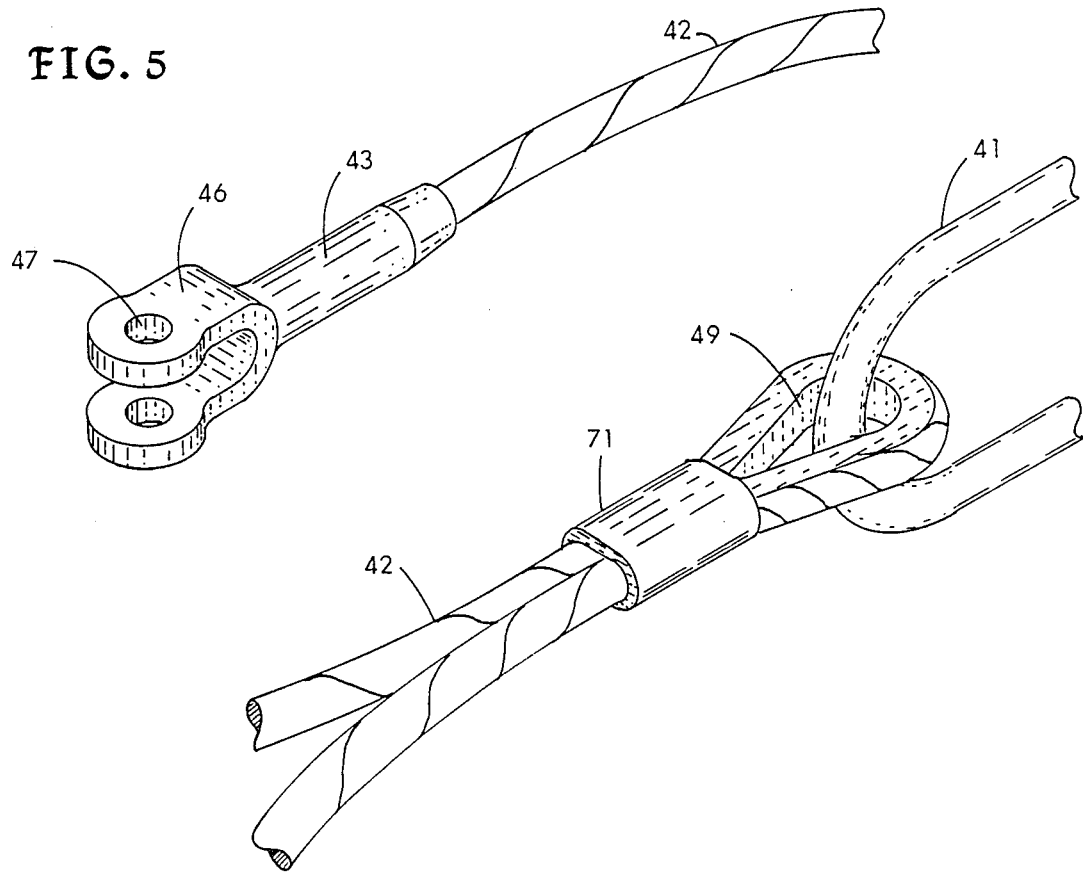
FIG. 5 is a partial respective view of both ends of the attachment cradle depicting the swedged lower fitting and the swedged upper fitting routing the cable about a cable thimble.

With reference to FIG. 5, it can be seen that cable sling 42 is provided with a swage socket 43 of the clevis type on the lower end. Swage socket 43 has an open socket 46 with a opening 47 to allow clevis pin 48 as depicted in FIG. 2 to be inserted to secure cable 42 to floor 22. The upper end of cable sling 42 is attached to master link 41 by passing cable 42 about thimble 49 and locking the cable in position by use of fitting 71. Cable 42 could be of any type of cable that is sufficiently strong and has been tested in accordance with applicable regulations. It is contemplated within the scope of the invention that the cable sling 42 to support manbasket 13 is comprised of two complete sets having four downwardly depending cable arms each terminating an open swage socket 43 for attachment to manbasket 13. Each cable set would be pretested and certified for use in transporting personnel in manbasket 13.

Figure 6:
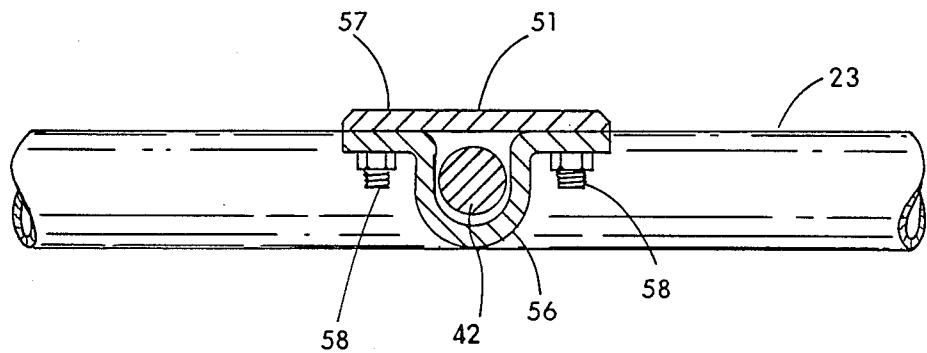
FIG. 6 is a partial top plan view of the cable fairlead on the upper handrail of the manbasket in accordance with the present invention.

With reference to FIG. 6, fairlead 51 is depicted in which cable 42 is routed through channel 56 vertically and is covered with end plate 57 which is attached to channel 42 by use of bolts 58 in a manner well known in the art. As shown in FIGS. 2, 3, and 4, fairlead 51 is also provided with elbow 52 so as to provide a smooth continuous channel for cable 42.

Figure 7:
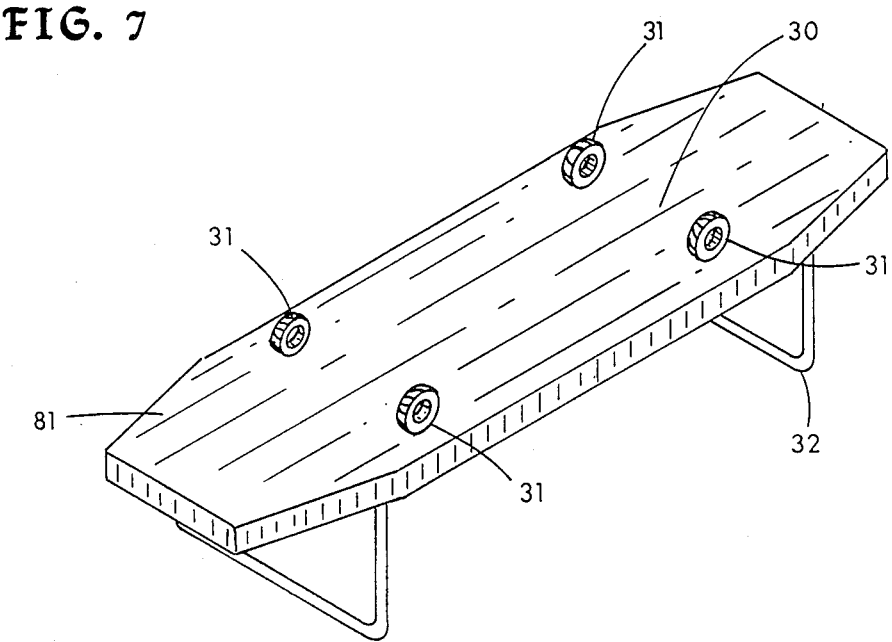
FIG. 7 is a perspective view of the test weight with attached support skid removed from the manbasket all in accordance with the present invention.

With reference to FIG. 7, it can be seen that test weight 30 having eyebolts 31 is attached o the upper surface 81. Test weight 30 is a block of material having a predetermined weight such as mild steel, lead, cast iron or the like. Test weight 30 is further provided with a support stand 32 which depends both downwardly and outwardly from the lower surface of test weight 31 and provides a sufficient base upon which test weight 30 can rest and yet maintains the height of the test weight 30 to a height at which eyes 31 will extend through the floor 22 of manbasket 13 so that attachment rod 61 can be inserted through eyes 31 for attachment of weight 32 of manbasket 13. By elongating test weight 30 and flatening it in the manner as shown in FIG. 7, the test weight 30 can be uniformly spread across floor 22 of manbasket 13 in the manner as required by OSHA in that the test weight 30 is evenly distributed. Although the eyes 31 extend through floor 22 as do attachment rods 61, the floor 22 would not be cluttered or obstructed when in use as the test weight 30 would not be attached when the manbasket 13 is used. By having the eyebolts extend through the floor, it is a convenient check to see that the test weight 30 has been detached prior to transporting personnel.

The method of use of the manbasket testing device of the instant invention will now be discussed. In order to employ the test weight, it is necessary only that it be attached to the manbasket. This is accomplished by having the crane operator position the manbasket 13 over test weight 30 so that eyes 31 extend through floor 22. The attachment rods 61 can then be slid through and inserted into eyes 31. Rod key lock 80 when engaged will keep rod 61 from inadvertently being removed. The manbasket 13 can then be lifted as depicted in FIG. 1 with weight 30 attached and the crane can then be positioned in all positions to which personnel could be hoisted. The manbasket 13 with attached test weight 30 as depicted in FIG. 1, can then be lowered to where testing weight support base 32 rests upon the ground. By twisting handle 62 90 degrees and disengaging key lock 80, attachment rod 61 can be removed. The manbasket then is raised and moved out of engagement with test weight 30 and the test weight with the particular configuration and boom lengths can be recorded according to the OSHA requirements. Personnel can then be safely transported. When it is necessary to move the manbasket and crane to another location, it is only necessary to reattach weight 30 by once again straddling weight 30 with manbasket 13, placing attachment rod 61 through eyes 31. The entire manbasket 13 and test weight 30 can then be moved to a new location where the next prelift test can be conducted.

Although specific applications, materials, components, connections, sequences of events, and methods have been stated in the above description of the preferred embodiment of the invention, other suitable materials, other applications, components and process steps as listed herein may be used with satisfactory results and varying degrees of quality. In addition, it will be understood that various other changes in details, materials, steps, arrangements of parts and uses which have been herein described and illustrated in order to explain the nature of the invention will occur to and may be made by those skilled in the art, upon a reading of this disclosure, and such changes are intended to be included within the principles and scope of this invention as hereinafter claimed.

I claim:

1. A manbasket testing apparatus comprising:
   a manbasket having a floor;
   sling means for suspending the manbasket from a crane, said sling means attached to the manbasket; and
   weight means removably attached to and positioned underneath the floor of the manbasket wherein said weight means is comprised of a fixed weight having an upper surface and wherein the upper surface of said weight provides attachment means for removably attaching said weight to said manbasket.

2. The manbasket testing apparatus as described in claim 1 wherein said fixed weight further comprises a weight base means attached to said weight and beneath said weight upon which said weigh rests.

3. The manbasket testing apparatus as described in claim 2 wherein said weight attachment means is comprised of eyebolts affixed to said fixed weight upper surface.

4. The manbasket testing apparatus as described in claim 3 further comprising an attachment rod having a first end and a second end, said rod insertably positioned within at least two of said eyebolts.

5. The manbasket testing apparatus as described in claim 4 further comprising a locking pin attached to said first end of said attachment rod.

6. The manbasket testing apparatus as described in claim 4 further comprising a handle attached to said second end of said rod.

7. The manbasket testing apparatus as described in claim 1 wherein said sling means is attached to said floor of said basket.

8. The manbasket testing apparatus as described in claim 7 further comprising a cable fairlead attached to said manbasket and through which said sling means passes.

9. The manbasket testing apparatus as described in claim 8 wherein said basket is provided with handrail means and wherein said fairlead is attached to said handrail means.

10. The manbasket testing apparatus as described in claim 9 further comprising smooth cable routing elbows attached to said fairleads.

11. The manbasket testing apparatus as described in claim 10 wherein said sling is comprised of four cables each of said cables attached to said floor of said manbasket and to said master link.

12. The manbasket testing apparatus as described in claim 11 wherein two of said four cables comprise a manbasket sling set.

13. The method of testing a manbasket comprising the steps of:
   providing a manbasket having a floor, a sling means attached to said basket and a weight means removably attached underneath and to said floor wherein said weight means is comprised of a fixed weight having an upper surface and wherein the upper surface of said weight provides attachment means for removably attaching said weight to said manbasket;
   attaching said weight means to said manbasket;
   raising said manbasket and suspending it for a period of time;
   lowering said manbasket testing device; and
   removing said weight means.

* * * * *